US008839792B2

(12) United States Patent
Brunner

(10) Patent No.: US 8,839,792 B2
(45) Date of Patent: Sep. 23, 2014

(54) CONDOM DEVICE

(71) Applicant: Pittsburgh AIDS Task Force, Pittsburgh, PA (US)

(72) Inventor: David T. Brunner, Pittsburgh, PA (US)

(73) Assignees: David Brunner, Pittsburgh, PA (US); Pittsburgh Aids Task Force, Pittsburgh, PA (US)

( * ) Notice: Subject to any disclaimer, the term of this patent is extended or adjusted under 35 U.S.C. 154(b) by 1 day.

(21) Appl. No.: 13/630,567

(22) Filed: Sep. 28, 2012

(65) Prior Publication Data

US 2014/0090650 A1  Apr. 3, 2014

(51) Int. Cl.
*A61F 6/02* (2006.01)
*A61F 6/04* (2006.01)
*A41D 19/00* (2006.01)
*A61F 5/44* (2006.01)
*A61F 5/453* (2006.01)

(52) U.S. Cl.
CPC . *A61F 5/453* (2013.01); *A61F 6/04* (2013.01); *A61F 2006/041* (2013.01); *Y10S 128/917* (2013.01); *Y10S 128/918* (2013.01)
USPC ........... 128/844; 128/842; 128/917; 128/918; 427/2.3; 604/346; 604/347

(58) Field of Classification Search
CPC ............. A61F 5/00; A61F 5/44; A61F 5/451; A61F 5/453; A61F 6/00; A61F 6/02; A61F 6/04
USPC .......... 128/842, 844, 917, 918; 604/346–353; 427/2.3; 600/38–41
See application file for complete search history.

(56) References Cited

U.S. PATENT DOCUMENTS

| 87,932 | A | * | 3/1869 | Hoffman | 604/349 |
| 3,759,254 | A | * | 9/1973 | Clark | 600/39 |
| 4,820,290 | A | | 4/1989 | Yahr | |
| 5,111,831 | A | * | 5/1992 | Foggia | 128/842 |
| 5,314,447 | A | * | 5/1994 | Papurt | 128/842 |
| 5,318,042 | A | * | 6/1994 | Gray | 128/844 |
| 5,351,699 | A | * | 10/1994 | Hammons | 128/844 |
| 5,718,236 | A | * | 2/1998 | Curcio | 128/844 |

(Continued)

OTHER PUBLICATIONS

"Latex Teat-End Penis Sheath", http://www.twistmyrubberarm.com/index.php?code=6023&k0=him; printed Nov. 1, 2012 (1 page)—Admitted Prior Art.

(Continued)

*Primary Examiner* — Patricia Bianco
*Assistant Examiner* — Brandon L Jackson
(74) *Attorney, Agent, or Firm* — Buchanan Ingersoll & Rooney PC

(57) ABSTRACT

An elastomeric condom device including a tubular portion to cover the shaft of the penis, the tubular portion having a first thickness; a pouch portion to cover the scrotum, the pouch portion having a second thickness; and a middle portion provided between the tubular and pouch portions, the middle portion having a thickness that is at least double the thickness of the thickest of the first and second thicknesses. The middle portion includes an opening for insertion of the penis and scrotum, the opening defined by an elastic ring of heavier construction than the middle portion, wherein when the condom is in place over the male genitalia the elastic ring is positioned around the base of the penis and the scrotum at the torso of the body.

17 Claims, 7 Drawing Sheets

(56) References Cited

U.S. PATENT DOCUMENTS

| | | | |
|---|---|---|---|
| 5,806,278 A | | 9/1998 | Shelledy |
| D400,247 S | * | 10/1998 | Landberg .................... D24/105 |
| 6,061,840 A | * | 5/2000 | Alligator ........................... 2/403 |
| 6,209,543 B1 | * | 4/2001 | Star .............................. 128/844 |
| 6,478,027 B1 | * | 11/2002 | Serrano et al. ................ 128/844 |
| 2005/0188995 A1 | * | 9/2005 | McCoy ........................ 128/844 |
| 2010/0071702 A1 | * | 3/2010 | Sturlingh ...................... 128/844 |

OTHER PUBLICATIONS

"Star Tech Condoms", http://startechintl.tripod.com; printed Nov. 1, 2012 (4 pages)—Admitted Prior Art.

"Oxballs Xtender", http://www.forttroff.com/73873_gallery?pcat=CSH; printed Nov. 1, 2012 (9 pages)—Admitted Prior Art.

* cited by examiner

CONDOM DEVICE

FIELD OF THE INVENTION

The present disclosure is generally directed toward condom or sheath devices designed to protect against venereal infection during sexual intercourse and pregnancy and, more particularly, toward condom or sheath devices providing such protection for the scrotum and penis areas, as well as having an improved fit and/or increased sensation and/or increased pleasure and/or enhanced erectile performance.

BACKGROUND OF THE INVENTION

The following disclosure for a condom was developed after more than a decade of working in the field of HIV prevention and discussing the limitations to traditional condoms with hundreds of people. Discussions have revealed that the most common issues that people report while using traditional condoms are the lack of sensation, the loss of spontaneity while opening and applying the condom after erection and before intercourse begins, and the difficulty of maintaining an erection while the condom is on. Aside from these frequently stated frustrations, there is the reality that traditional condoms are able to slide off during intercourse (such that it can allow the passage of bodily fluid between sexual partners). Typically, the condom is prone to sliding off when the penis is removed from the sexual partner; however, the condom can slide off during intercourse as well leaving partners at greater risk for pregnancy or sexually transmitted diseases ("STDs"). Another limitation to condoms prevention of STDs is that traditional condoms only coved the shaft of the penis, which leaves the base of the penis and the scrotum vulnerable to STDs such as, for example, Syphilis, Herpes, HPV (which can cause genital warts), and other diseases which can be spread through physical contact with the penis or scrotum.

HIV and other STDs continue to ravage the world. Lives continue to be lost and the costs of treating those infected have the potential of destabilizing states and nations. Unplanned pregnancies also have dramatically negative effects on society and the global population. The development of a condom that addresses all of the barriers to consistent condom use will be a great leap forward in addressing a number of global crises. Aside from these important local and global issues, the condom device of the present disclosure will be a great addition to the condom industry adding customers who traditionally do not enjoy using condoms into their consumer base and ultimately creating thousands of new jobs and stimulating the economy.

The present disclosure is directed toward overcoming one or more of the above-identified problems.

SUMMARY OF THE INVENTION

A condom device in accordance with the present invention is disclosed. The condom device includes a tubular portion to cover the shaft of the penis, the tubular portion having a first thickness; a pouch portion to cover the scrotum, the pouch portion having a second thickness; and a middle portion provided between the tubular and pouch portions, the middle portion having a thickness that is greater than both the first and second thicknesses, wherein the middle portion includes an opening for insertion of the penis and scrotum.

In one form, the thickness of the middle portion is at least double the thickness of the thickest of the first and second thicknesses.

In a further form, the middle portion includes an opening defined by an elastic ring of heavier construction than the middle portion, wherein when the condom is held in place over the male genitalia the elastic ring is positioned around the base of the penis and the scrotum at the torso of the body.

In yet a further form, the condom device is made of an elastomeric material.

In still a further form, the first and second thicknesses are the same, and wherein the thickness of the middle portion is at least double the thickness of the first/second portion.

When the condom is in place over the male genitalia the middle portion separates the tubular and pouch portions and fits around the portion of the body between the penis and the scrotum.

In another form, the tubular, pouch and middle portions may be formed as an integral elastomeric sheath. The tubular and pouch portions may be axially aligned, perpendicularly aligned, or angularly aligned.

An elastomeric condom device in accordance with an exemplary embodiment of the present invention is disclosed. The condom device includes a tubular portion to cover the shaft of the penis, the tubular portion having a first thickness; a pouch portion to cover the scrotum, the pouch portion having a second thickness; and a middle portion provided between the tubular and pouch portions, the middle portion having a thickness that is at least double the thickness of the thickest of the first and second thicknesses. The middle portion includes an opening for insertion of the penis and scrotum, the opening defined by an elastic ring of heavier construction than the middle portion, wherein when the condom is in place over the male genitalia the elastic ring is positioned around the base of the penis and the scrotum at the torso of the body.

In one form, the first and second thicknesses are the same.

In another form, the tubular, pouch and middle portions may be formed as an integral sheath. The tubular and pouch portions may be axially aligned, perpendicularly aligned, or angularly aligned.

It is an object of the present disclosure to provide an improved condom device that protects against STDs while providing sexual satisfaction to a wearer in terms of at least one of improved sensation, enhanced erectile function, increased spontaneity, etc.

Various other objects, aspects and advantages of the present disclosure can be obtained from a study of the specification, the drawings, and the appended claims.

BRIEF DESCRIPTION OF THE DRAWINGS

Further possible embodiments are shown in the drawings. The present invention is explained in the following in greater detail as an example, with reference to exemplary embodiments depicted in drawings. In the drawings.

DETAILED DESCRIPTION OF THE INVENTION

Figure 5:
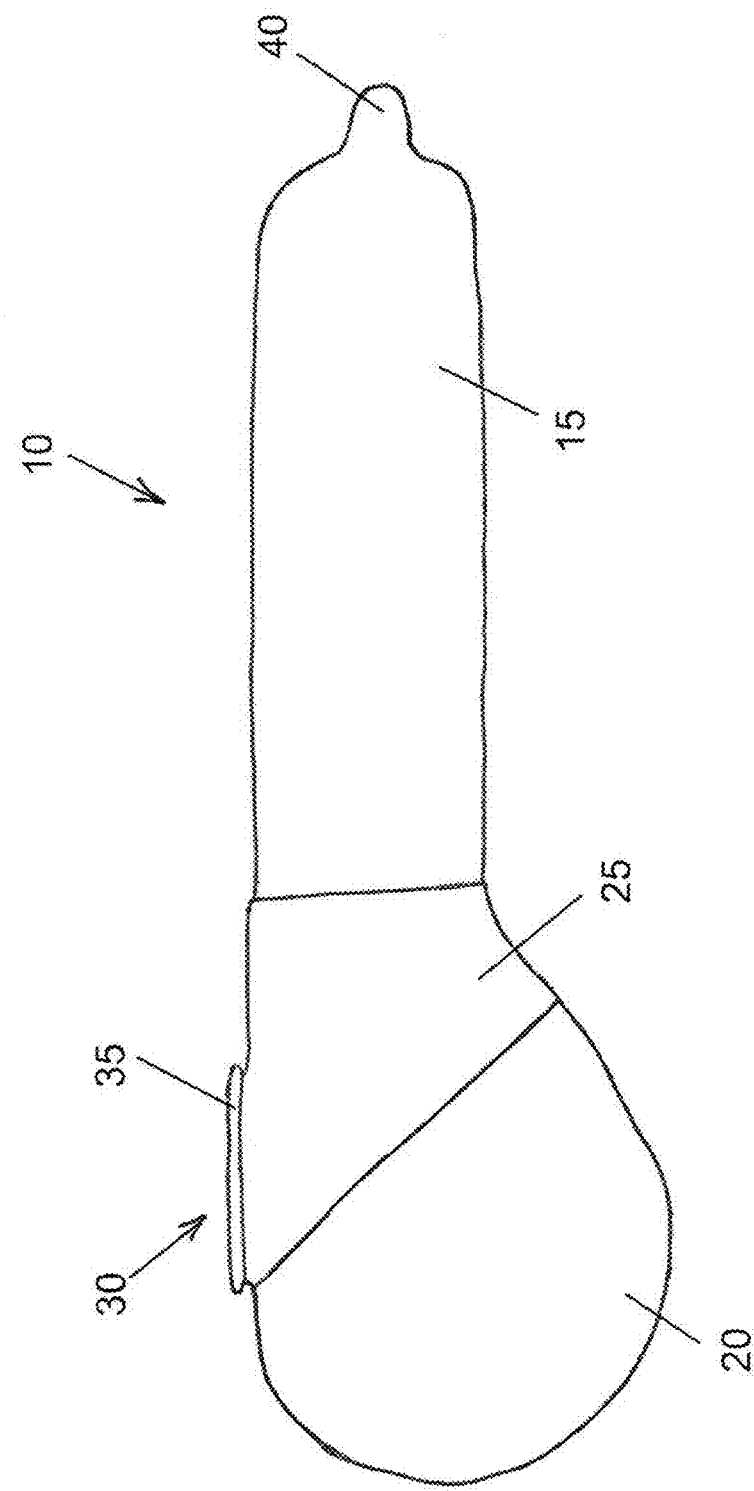
FIG. 5 is a side view of a fifth embodiment of a condom device in accordance with the present disclosure.
Figure 6:
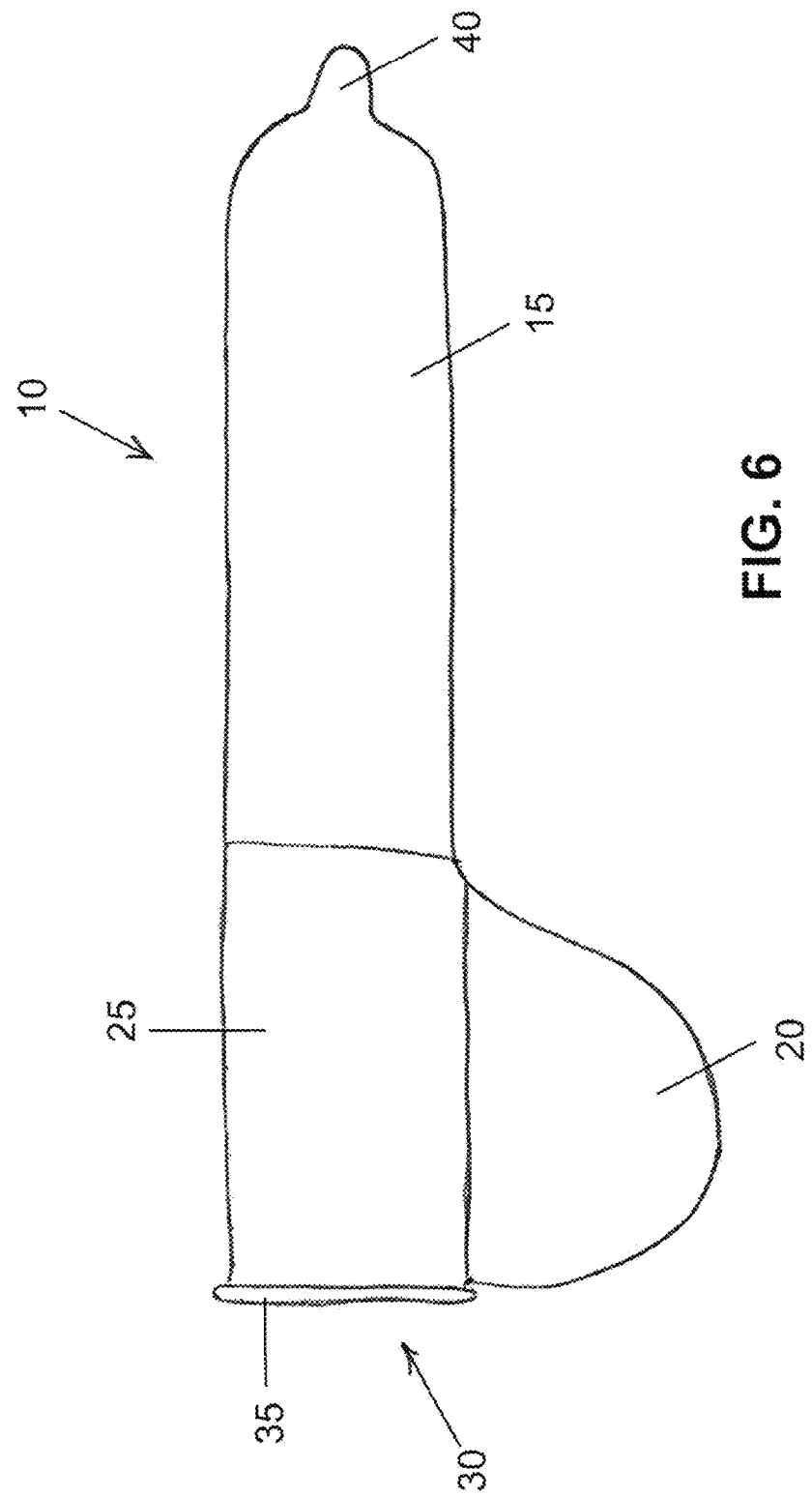
FIG. 6 is a side view of a sixth embodiment of a condom device in accordance with the present disclosure.
Figure 7:
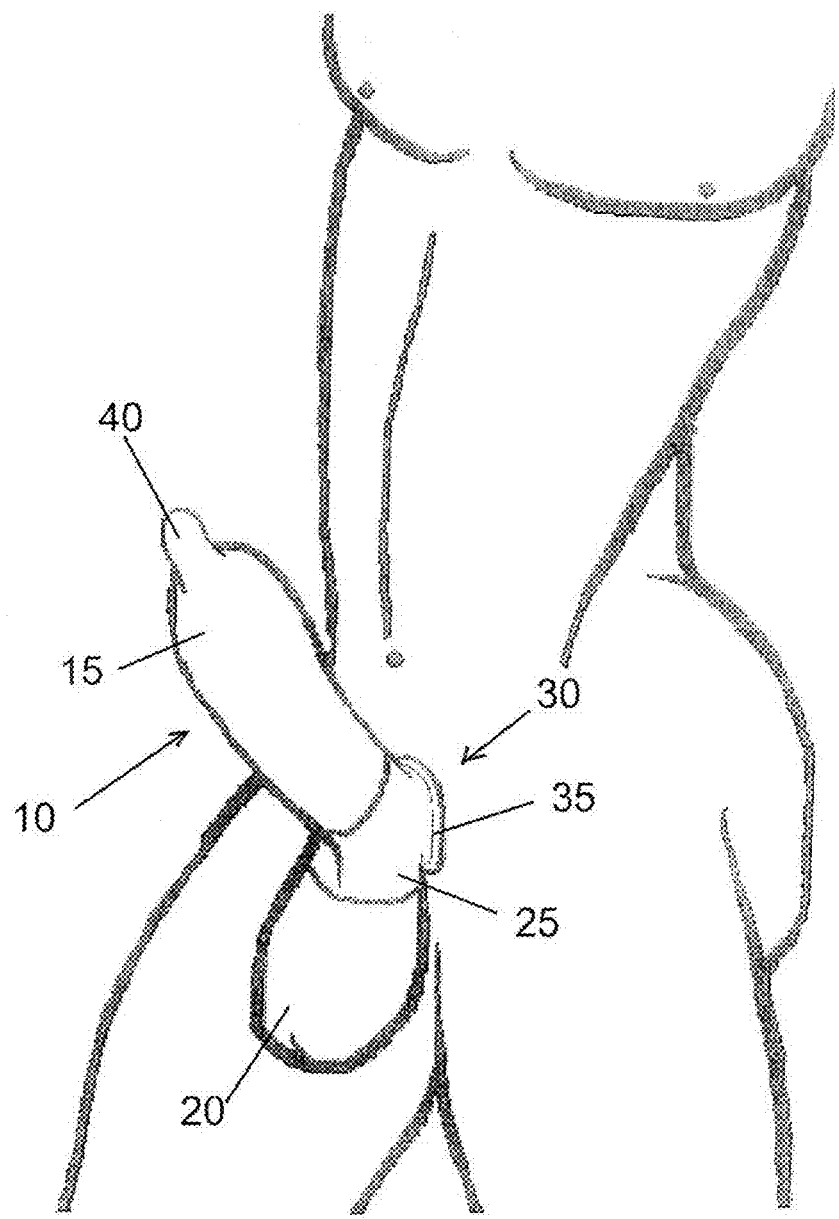
FIG. 7 is a perspective view of a condom device in accordance with the present disclosure fully unrolled and covering the penis and the scrotum and secured in place between the scrotum and the torso of a wearer.

As shown in FIGS. 1-7, a condom according to the present disclosure is generally shown at 10. The condom 10 is designed to fit over the head of the penis, the penis shaft and the scrotum. FIG. 7, which illustrates the condom 10 being worn by a user, is illustrative of how the various exemplary embodiments described herein will fit when worn by a user.

The condom 10 of the present disclosure is a generally thin-walled condom device having a generally tubular construction and includes a single, continuous elastic sheath. Of course, the condom 10 may be formed of a multi-part construction in accordance with the present invention.

The condom 10 includes a generally tubular portion 15 designed to cover the head and shaft of a penis. The condom 10 also includes a pouch portion 20 designed to cover the scrotum. Connecting the tubular portion 15 and the pouch portion is a middle portion 25. An open end 30 is provided in the middle portion 25 for applying the condom 10 to a penis. When the condom 10 is in place over the male genitalia, the tubular portion 15 covers the penis from the base to the head and the pouch portion 20 covers the entire scrotum. The middle portion 25 separates the tubular 15 and pouch 20 portions and, when the condom 10 is worn by a user, fits generally around the portion of the body between the base of the penis and the scrotum (see FIG. 7). The middle portion 25 made be formed integral with the tubular 15 and pouch 20 portions, or the various portions may be of a multi-part construction.

In order to provide a secure fit, the middle portion 25 is made thicker than the tubular 15 and pouch 20 portions and acts as a reinforcing portion of sorts. The middle portion 25 will flex the most when the condom 10 is put on and, thus, needs to be stronger. In a preferred embodiment, the middle portion 25 is approximately double the thickness of the tubular 15 and pouch 20 portions, with the tubular 15 and pouch 20 portions being of the same thickness. However, the tubular 15 and pouch 20 portions need not be the same thickness, and other thicknesses are contemplated, as long as the middle portion 25 is formed with a thickness that is thicker than the thickest of the tubular 15 and pouch 20 portions. For example, the middle portion 25 can, in one exemplary embodiment, be made approximately double the thickness of the thicker of the tubular 15 and pouch 20 portions.

The condom 10 includes an opening 30 formed in the middle portion 25, which opening 30 is defined by an integral elastic ring 35 formed of a heavier construction than the middle portion 25. The elastic ring 35 is stretched, along with the middle portion 25, and pulled over the male genitalia such that the scrotum is tucked into the pouch portion 20 and the elastic ring 35 is pulled and positioned between the scrotum and the torso of a wearer to secure the condom 10 in place (see FIG. 7). The elastic ring 35, as well as the middle portion 25, aid in putting on the condom 10. The tubular portion 15 may include a reservoir 40 at the distal tip for ejaculate.

As previously noted, when the condom is worn, the tubular portion 15 covers the head and shaft of the penis, the pouch portion 20 covers the scrotum, and the middle portion 25 separates the tubular 15 and pouch 20 portions and fits generally around the portion of the body between the base of the penis and the scrotum (see FIG. 7). Such a construction provides a secure fit, such that the condom 10 should not come off during sexual intercourse and even may be applied to the male anatomy well before sexual arousal. Additionally, since the elastic ring 35 is designed to be positioned around the base of the penis and the scrotum at the torso of the body, increased erectile performance may also result.

Figure 1:
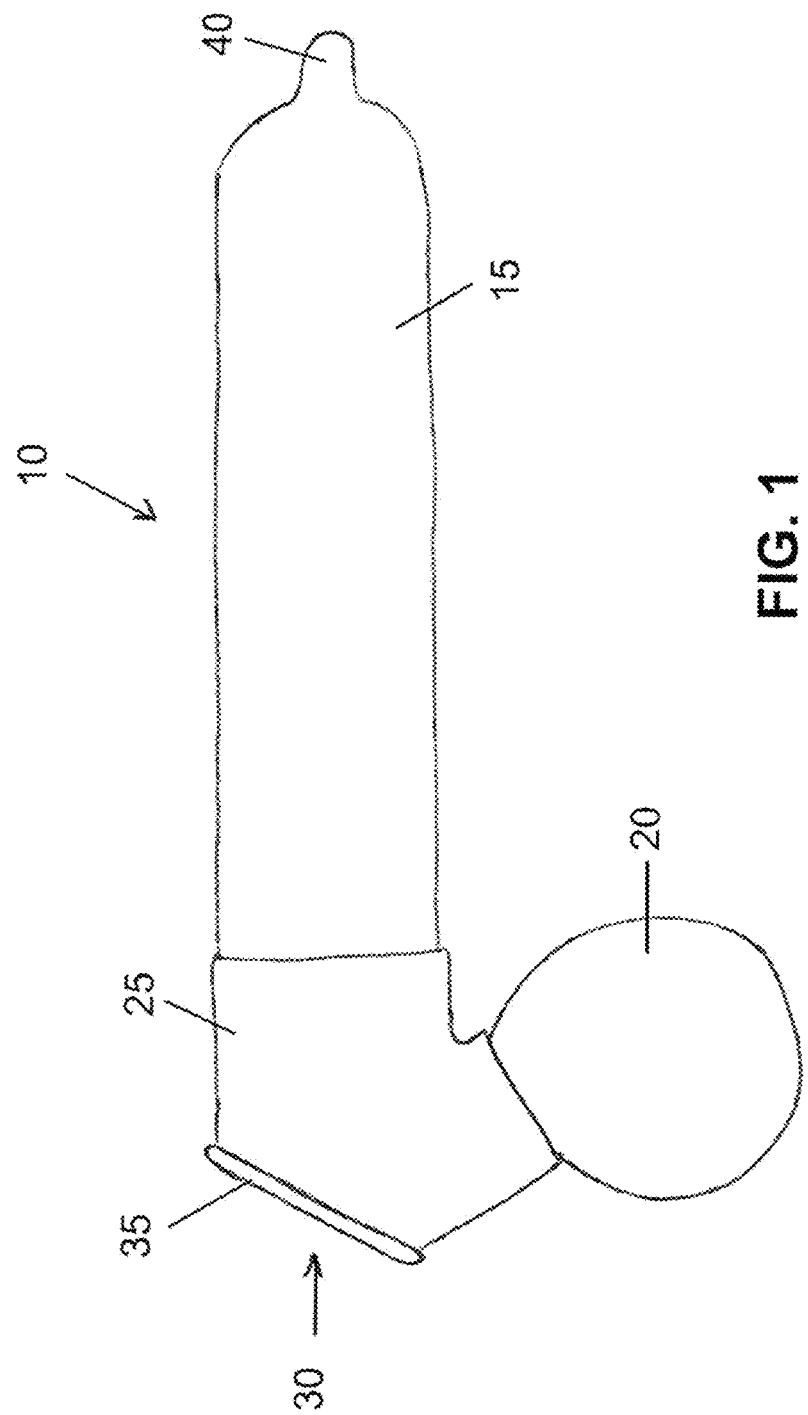
FIG. 1 is a side view of a first embodiment of a condom device in accordance with the present disclosure.
Figure 2:
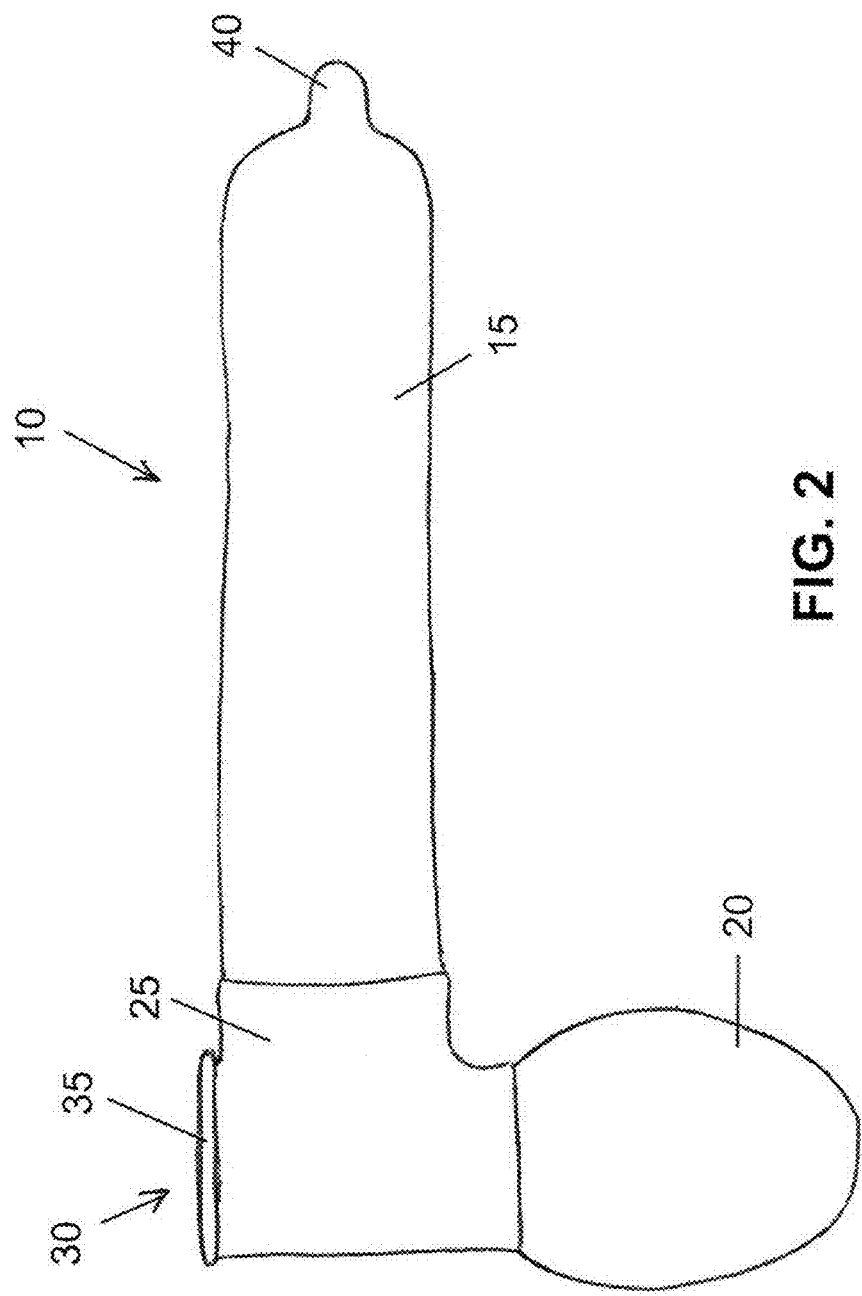
FIG. 2 is a side view of a second embodiment of a condom device in accordance with the present disclosure.
Figure 3:
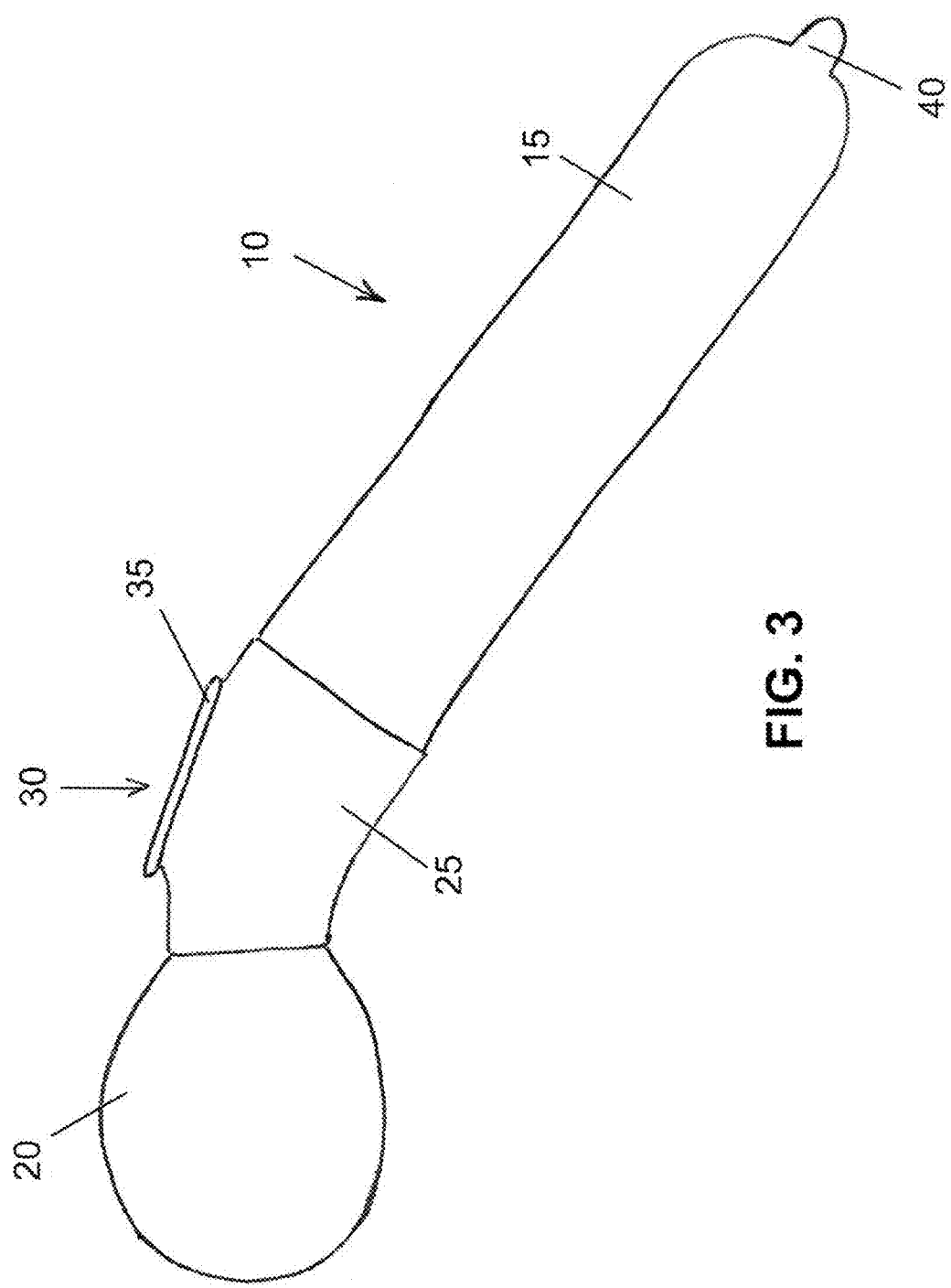
FIG. 3 is a side view of a third embodiment of a condom device in accordance with the present disclosure.
Figure 4:
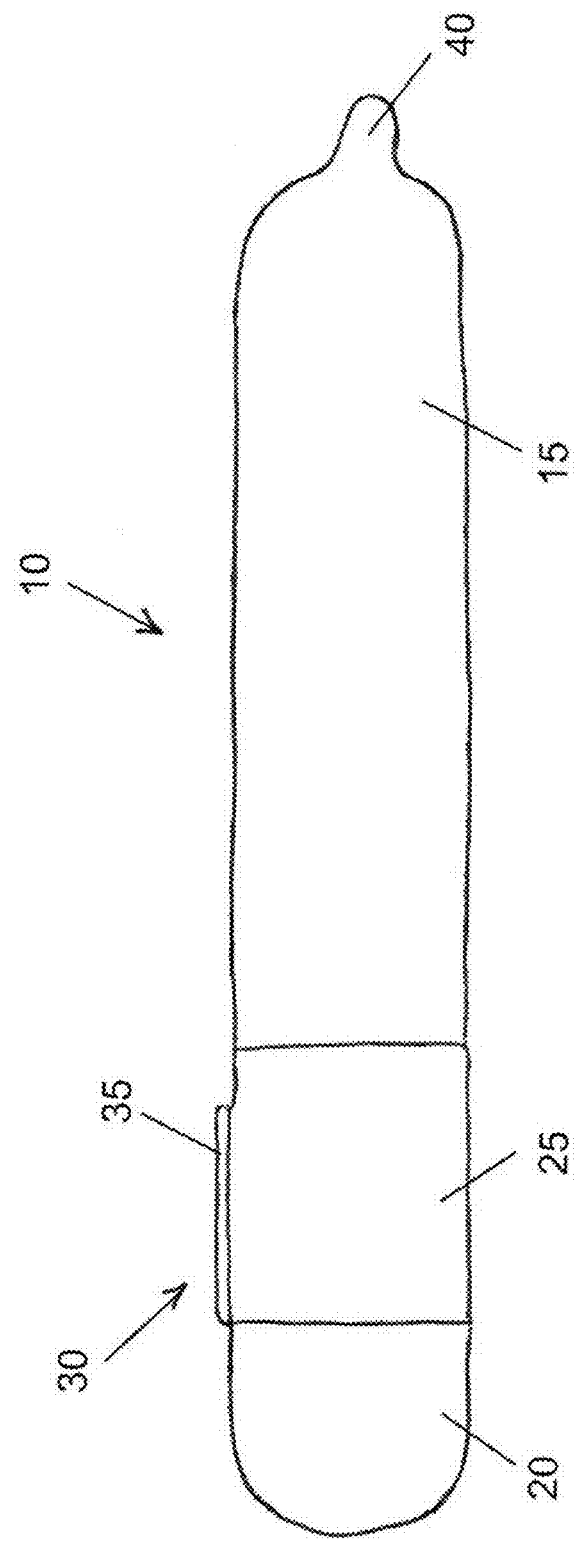
FIG. 4 is a side view of a fourth embodiment of a condom device in accordance with the present disclosure.

As shown in the Figures, the pouch portion 20 may be formed at various relationships to the tubular portion 15. For example, the pouch portion 20 may be formed: approximately perpendicular to the tubular portion 15 (as shown in FIGS. 2 and 6); at an angle to the tubular portion 15 (as shown in FIGS. 1, 3 and 5); or axial with the tubular portion 15 (as shown in FIG. 4). Additionally, the opening 30 may be formed at various relationships (e.g., perpendicular, angled, axial, etc.) to the tubular 15 and pouch 20 portions. The embodiments shown in the Figures are exemplary only and in no way limit the scope of any claim coverage herein.

As will be understood, the condom 10 (including the tubular portion 15, pouch portion 20, middle portion 25 and elastic ring 35) is made of an elastomeric material. As used herein, the term "elastomeric" is used in reference to thermoplastic materials useful for forming condom articles in accordance with the present invention, and generally means a material which subsequent to elongation thereof under an applied tensional force, regains at least a significant portion of its original dimensional characteristics when the applied tensional force is released. Suitable elastomeric materials for use in making condoms of the present invention include, but are not limited to, latex, polyisoprene, silicone, polyurethane materials such as, for example, polyester-based polyurethanes, polyester elastomers, block copolymers of polybutylene terephthalate and long chain polyether glycol, polyether block amides rubber based copolymers, ethylene-octene copolymers, as well as any other suitable homopolymers and copolymers and mixtures thereof and other materials suitable for condom use.

With respect to the above description, it is to be understood that the optimum dimensional relationships and physical properties for the parts of the inventive condom 10, to include variations in, for example, size, materials, shape, form, thickness, Shore hardness, tensile strength, elongation modulus, flexural modulus, specific gravity, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the present inventive condom 10 shown and described herein. Further, since numerous modifications and changes will readily occur to those skilled in the art, it is not desired to limit the present invention to the exact construction and operation shown and described and, accordingly, all suitable modifications and equivalents may be resorted to, falling within the spirit and scope of the present invention.

The inventive condom design shown and described herein will have a multi-faceted appeal to condom users, as well as to those who don't regularly use condoms, if at all. By addressing the pitfalls of erectile dysfunction, loss of spontaneity, decreased sensation, slippage, and inadequate STD prevention that traditional condoms have, the inventive condom design shown and described herein will enjoy many advantages.

Since the condom 10 is placed over the penis and the scrotum, it grips around both the base of the penis and the scrotum where the two meet the body. This is the same place where certain types of erectile enhancement apparatus are typically placed when an individual is seeking to increase their erectile performance. Thus, in addition to prevent the spread of STDs, the inventive condom 10 can also assist those who cannot maintain an erection, either with or without a traditional condom.

Further, with the condom 10 attaching at the base of the penis and scrotum, the condom 10 is also able to be applied even before an erection occurs, and even hours before the onset of coitus. This eliminates any issues relating to spontaneity that people experience while fumbling in the dark for a traditional condom during their most passionate moments.

Also, unlike a traditional condom, the inventive condom 10 can have lubricant on the inside allowing the condom 10 to glide up and down the penis shaft giving increased and enhanced sensation to the user. This could additionally include textures inside the condom 10 to further enhance the pleasure of the user. The condom 10 can also include lubricants and/or spermicides, as well as various textures, on the outside of the condom 10 to further enhance the pleasure of a user's sexual partner. Since the condom 10 is held on at the base of the penis and scrotum, it will not slide off during intercourse, even as the possible gliding motion (e.g., the condom 10 gliding up and down the penis shaft) is occurring. The sensations possible with this new design will also create a new market for the condom 10 as a pleasurable device for individuals during oral intercourse or even while masturbating.

By making condoms more pleasurable and user friendly, the present invention will increase condom usage and, in turn, help reduce the spread of STDs. The inventive condom 10 will also increase protection for consistent traditional condom users as well. For example, Syphilis, Herpes and HPV (which can cause genital warts) are all spread through physical skin-to-skin contact. A Herpes sore, a Syphilis sore, or Genital wart, could be present on the skin of the scrotum of a male, or on or around the inner thigh of the receptive partner. By having a protective portion covering the scrotum and the base of the penis, which traditional condoms leave uncovered and exposed, the new condom will give extra protection against these and other skin-to-skin contact diseases. A further benefit is that the inventive condom 10 will not slide off, which can happen with a traditional condom.

With all of these advantages, the inventive condom design will hopefully give new rise and enthusiasm around STD and pregnancy prevention and condom use.

One skilled in the art will appreciate that the condom device of the present disclosure may take many different shapes, sizes, materials, thicknesses, flavors and textures without departing from the spirit and scope of the present invention. Of course, for proper application and usefulness, the condom device of the present invention should include one, some or all of the following features:

The condom should be made of a flexible, non-permeable material such as, for example, latex, polyisoprene, polyurethane, etc.

The condom should have a reservoir tip where semen can collect.

The condom should cover the entire penis and scrotum with the opening at the base where the scrotum and penis meet the torso/body.

The condom should have a portion to accommodate the scrotum.

The condom should have an extra thick portion from the area close to where the penis meets the opening of the condom and encompassing the portion of the condom that needs to be stretched in order to be applied. This may or may not include some, or the entire, portion that covers the scrotum. This is to provide extra durability to the portion of the condom that will be stretched during application.

Additionally, one skilled in the art will appreciate that many variations of the condom device of the present invention are possible without departing from the spirit and scope of the present invention. These variations can include, but are not limited to, the following variations which can be implemented singularly or in combination:

Different materials for the condom such as, for example, latex, polyisoprene, polyurethane, etc., or any combination thereof.

Various thicknesses of the condom including, but not limited to, the thickness of the opening.

Various lengths and widths of the condom, as well as various sizes of the scrotum covering portion.

Various sizes of the opening of the condom.

Various configurations of the condom as shown, but not limited to, the attached drawings, which are to be considered and exemplary only.

Various textures inside the condom that can enhance pleasure.

Various textures outside the condom that can enhance pleasure.

Different shapes of the condom like, for example, a pouch near the tip with ridges inside to give more pleasure to the head of the penis.

Various lubricants used with the condom such as, but not limited to, water-based lubricants, silicone-based lubricants, microbicide gels, flavored lubricants, heating or cooling sensation lubricants, etc.

Various colors and visual variations like, for example, glowing variations, for the condom.

Various attachments to the condom like, for example, vibrating rings, etc.

Various non-harmful scents applied to the condom like, for example, perfumes, pheromones, etc.

Virtually any other variation to the condom as well.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

I claim:

1. A condom device comprising:
  a tubular portion to cover the shaft of the penis, the tubular portion having a first thickness and the tubular portion having a first end and a second end;
  a pouch portion to cover the scrotum, the pouch portion having a second thickness, and the pouch portion having a first end and a second end; and
  a middle portion provided between the tubular and pouch portions, the middle portion having a first end, a second end, and an opening, the first end of the middle portion being connected to the first end of the tubular portion, the second end of the middle portion being connected to the first end of the pouch portion; and
  wherein the middle portion has a thickness that is greater than the first thickness and the second thickness; and
  wherein the middle portion includes the opening for insertion of the penis and scrotum; and wherein an elastic ring is connected to the middle portion, the integral elastic ring being of heavier construction than the middle portion and defining the opening.

2. The condom device of claim 1, wherein the first and second thicknesses are the same.

3. The condom device of claim 2, wherein the thickness of the middle portion is at least double the thickness of at least one of the tubular portion and the pouch portion.

4. The condom device of claim 1, wherein the thickness of the middle portion is at least double the thickness of the thickest of the first and second thicknesses.

5. The condom device of claim 1, wherein the elastic ring is configured such that when the condom is in place over the male genitalia the elastic ring is positioned around the base of the penis and the scrotum at the torso of the body.

6. The condom device of claim 1, wherein the condom device is made of an elastomeric material.

7. The condom device of claim 1, wherein when the condom is in place over the male genitalia the middle portion separates the tubular and pouch portions and fits around the portion of the body between the penis and the scrotum.

8. The condom device of claim 1, wherein the tubular, pouch and middle portions are formed as an integral elastomeric sheath.

9. The condom device of claim 1, wherein the tubular and pouch portions are axially aligned.

10. The condom device of claim 1, wherein the tubular and pouch portions are perpendicularly aligned.

11. The condom device of claim 1, wherein the second end of the tubular portion comprises a reservoir.

12. An elastomeric condom device comprising:
a tubular portion to cover the shaft of the penis, the tubular portion having a first thickness and the tubular portion having a first end and a second end;
a pouch portion to cover the scrotum, the pouch portion having a second thickness, and the pouch portion having a first end and a second end; and
a middle portion provided between the tubular and pouch portions, the middle portion having a first end, a second end, and an opening, the first end of the middle portion being connected to the first end of the tubular portion, the second end of the middle portion being connected to the first end of the pouch portion; and
wherein the middle portion has a thickness that is at least double the thickness of the thickest of the first and second thicknesses; and
wherein the middle portion includes the opening for insertion of the penis and scrotum, the opening defined by an elastic ring of heavier construction than the middle portion, wherein when the condom is in place over the male genitalia the elastic ring is positioned around the base of the penis and the scrotum at the torso of the body.

13. The condom device of claim 12, wherein the first and second thicknesses are the same.

14. The condom device of claim 12, wherein the tubular, pouch and middle portions are formed as an integral sheath.

15. The condom device of claim 12, wherein the tubular and pouch portions are axially aligned.

16. The condom device of claim 12, wherein the tubular and pouch portions are perpendicularly aligned.

17. The condom device of claim 12, wherein the second end of the tubular portion comprises a reservoir.

* * * * *